(12) United States Patent
Pei

(10) Patent No.: US 8,855,760 B2
(45) Date of Patent: Oct. 7, 2014

(54) SYSTEMS AND METHODS FOR EARLY DETECTION OF LEAD BREACHES USING CROSS-LEAD IMPEDANCES DETECTED BY AN IMPLANTABLE MEDICAL DEVICE

(71) Applicant: Pacesetter, Inc., Sylmar, CA (US)

(72) Inventor: Xing Pei, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 14 days.

(21) Appl. No.: 13/675,918

(22) Filed: Nov. 13, 2012

(65) Prior Publication Data

US 2014/0135860 A1     May 15, 2014

(51) Int. Cl.
  *A61N 1/08* (2006.01)
  *A61N 1/362* (2006.01)
  *A61N 1/39* (2006.01)

(52) U.S. Cl.
  CPC ............ *A61N 1/3937* (2013.01); *A61N 1/3622* (2013.01)
  USPC ..................................... 607/4; 607/8; 607/27

(58) Field of Classification Search
  CPC ..... A61N 1/37; A61N 1/3706; A61N 1/3962; A61N 1/3622; A61N 1/3937; A61N 1/3943
  USPC ................................................... 607/4, 8, 27
  See application file for complete search history.

(56) References Cited

U.S. PATENT DOCUMENTS

| 5,755,742 | A | * | 5/1998 | Schuelke et al. ................. 607/27 |
| 7,272,436 | B2 | | 9/2007 | Gill et al. |
| 7,454,249 | B1 | | 11/2008 | Bornzin et al. |
| 7,991,472 | B2 | | 8/2011 | Levine et al. |
| 2009/0299421 | A1 | | 12/2009 | Sawchuk |
| 2010/0286541 | A1 | | 11/2010 | Musley et al. |
| 2011/0054554 | A1 | | 3/2011 | Swerdlow |
| 2012/0035493 | A1 | | 2/2012 | Gutfinger et al. |
| 2012/0035495 | A1 | | 2/2012 | Gutfinger et al. |
| 2012/0078320 | A1 | | 3/2012 | Schotzko et al. |
| 2012/0191153 | A1 | * | 7/2012 | Swerdlow et al. ................. 607/8 |

FOREIGN PATENT DOCUMENTS

| WO | 2009148427 A1 | 12/2009 |
| WO | 2012044370 A1 | 4/2012 |
| WO | 2012054100 A1 | 4/2012 |

* cited by examiner

*Primary Examiner* — Christopher D Koharski
*Assistant Examiner* — Michael Carey

(57) ABSTRACT

Techniques are provided for use with an implantable medical device for detecting breaches in lead insulation or other lead failures. In one example, bipolar impedance is measured along single-lead vectors (i.e. intra-lead vectors) of a right atrial (RA) lead and a right ventricular (RV) leads. Impedance is also measured along various cross-lead vectors (i.e. inter-lead vectors) between electrodes of the two leads. A derived impedance value is then determined from a combination of the measured impedance values, wherein the derived impedance is sensitive to a shunt impedance arising from a breach within the RV lead. A lead breach is then detected relatively early based on the derived impedance by detecting a significant deviation in derived impedance over time. Unipolar impedance measurements are used to confirm the breach.

19 Claims, 8 Drawing Sheets

```
┌─────────────────────────────────────────────────────┐
│       EXEMPLARY RV BIPOLAR LEAD BREACH DETECTION    │
└─────────────────────────────────────────────────────┘
                         │
                         ▼
```

MEASURE SINGLE-LEAD (I.E. INTRA-LEAD) IMPEDANCES FOR BOTH THE RIGHT ATRIAL (RA) LEAD AND RIGHT VENTRICULAR (RV) LEAD -- ($M(RA_{BI})$ AND $M(RV_{BI})$) -- WHERE:

$M(RA_{BI}) = (RA_{TIP} - RA_{RING})$ AND
$M(RV_{BI}) = (RV_{TIP} - RV_{RING})$

200

MEASURE SELECTED CROSS-LEAD (I.E. INTER-LEAD) IMPEDANCES BETWEEN THE RV AND RA LEADS -- M1, M2, M3, AND M4 -- WHERE:

$M1 = (RA_{RING} - RV_{RING})$
$M2 = (RA_{RING} - RV_{TIP})$
$M3 = (RA_{TIP} - RV_{RING})$
$M4 = (RA_{TIP} - RV_{TIP})$

202

CALCULATE, DETERMINE OR OTHERWISE GENERATE A DERIVED IMPEDANCE D WHERE:

$D = SUM(M1, M2, M3, M4) - 2*(M(RA_{BI}) + (M(RV_{BI}))$

204

MEASURE UNIPOLAR IMPEDANCES ($U_I$) FOR SOME OR ALL OF THE AVAILABLE ELECTRODES TO THE CAN (I.E. THE DEVICE HOUSING)

212

RECORD AND TRACK VALUES FOR D AND U OVER TIME (SUCH AS ONCE PER DAY OVER AT LEAST A 30 DAY INTERVAL) TO DETECT TRENDS IN D AND U

FIG. 3A

SYSTEMS AND METHODS FOR EARLY DETECTION OF LEAD BREACHES USING CROSS-LEAD IMPEDANCES DETECTED BY AN IMPLANTABLE MEDICAL DEVICE

FIELD OF THE INVENTION

The invention generally relates to Implantable Cardiac Rhythm Management Devices (CRMDs) and, in particular, to techniques for detecting insulation breaches within leads connected to the devices.

BACKGROUND OF THE INVENTION

A wide range of implantable medical devices are provided for surgical implantation within patients, such as cardiac pacemakers, implantable cardioverter defibrillators (ICDs), cardiac resynchronization therapy (CRT) devices or other implantable cardiac rhythm management devices (CRMDs.) Typically, such devices are equipped with one more leads for sensing electrical signals such as cardiac signals. However problems can arise if an insulation breach occurs in the lead, potentially exposing one of its internal conducting wires to blood or other patient tissues, yielding a form of short circuit that interferes with the capability of the lead to properly sense cardiac signals and delivery appropriate therapeutic pulses, as well as resulting false sensing leading to inappropriate therapy. For example, some bipolar leads include a central wire for connecting a first electrical terminal of the CRMD to a tip electrode at the distal end of the lead. An outer coaxial conductor is provided for connecting a second electrical terminal (of opposite polarity) to a ring electrode, which is mounted near the tip electrode. An outer insulating sheath surrounds the ring conductor to isolate it from blood and other patient tissues. In use, however, the sheath can abrade, eventually exposing the ring conductor to patient tissues. Similar problems can occur in "flat wire" leads as well. Abrasion or other lead failures can cause: impropriate therapy due to false over-sensing; withheld therapy due to under-sensing or over-sensing (inhibition); failure to deliver therapy due to due to conductor failures; damage to the device itself, etc. Long term reliability of CRMD leads is a key factor clinicians consider when selecting particular cardiac systems for implant within patients.

Although lead reliability has improved dramatically over the years, leads can still fail for various reasons. Accordingly it would be desirable to provide techniques for early detection of the lead failures so that leads can be replaced before complete failure occurs. This would provide valuable protection to patients and additional assurances to the healthcare providers. Typically, to detect a lead failure using a CRMD system with a bipolar lead, impedances are measured between tip and ring electrodes of the bipolar lead. If the bipolar impedance drifts out of range or fluctuates more than expected, such indicates the lead may be experiencing a fracture. However, this technique may not be sensitive enough for early detection of lead integrity issues arising due to insulation breach because the impedance change may still be relatively small.

SUMMARY OF THE INVENTION

In one embodiment, a method is provided for use with an implantable medical device having a lead system with at least two leads each having a plurality of electrodes, such as a system employing right ventricular (RV) and right atrial (RA) bipolar leads. In one example, values representative of impedance are measured along various single-lead vectors (i.e. intra-lead vectors) between pairs of electrodes of each individual lead, such as between the tip and ring electrodes of the RV lead and between the tip and ring electrodes of the RA lead. Values representative of impedance are also measured along various cross-lead vectors (i.e. inter-lead vectors) between electrodes of different leads, such as between the tip of the RV lead and the ring of the RA. A derived impedance value is then determined from a combination of the measured values wherein the derived impedance is sensitive to a shunt impedance arising from a breach within one of the leads. An indication of a possible lead breach is then detected based on the derived impedance by detecting a significant deviation in the derived impedance over time. In this regard, certain cross-lead impedance vectors can change direction when there is an insulation breach since the breach point shunts impedance. As such, a derived impedance generated to emphasize such changes in impedance vector direction can be sensitive to small changes in impedance arising due to abrasion of the lead insulation. Hence, the technique is well-suited for detecting lead breeches relatively early to allow replacement of the lead before a more complete lead failure occurs that would likely interfere with signal sensing or therapy delivery.

In an illustrative example, the technique is used by a CRMD to detect a lead breach occurring within a middle portion of a bipolar RV lead based on a deviation in the derived impedance obtained from a combination of single-lead RA and RV impedances and various cross-lead RA-RV impedances. To obtain single-lead impedance measurements, the CRMD measures impedance values $M(RA_{Bi})$ representative of impedance between tip and ring electrodes of the right atrial lead (i.e. RA tip-RA ring) and also measures impedance values $M(RV_{Bi})$ representative of impedance between tip and ring electrodes of the RV lead (i.e. RV tip-RV ring). To obtain cross-lead impedance measurements, the CRMD measures: M1 values representative of impedance between RA tip and RV ring electrodes; M2 values representative of impedance between RA ring and RV tip electrodes; M3 values representative of impedance between RA tip and RV ring electrodes; and M4 values representative of impedance between RA tip and RV tip electrodes. The CRMD determines derived impedance (D) using:

$$D = \text{SUM}(M1, M2, M3, M4) - 2*(M(RA_{Bi}) + M(RV_{Bi})).$$

The CRMD then detects a possible lead breach based on a significant deviation in derived impedance (D) over time. In one particular example, the CRMD: determines a variation (SD) in the derived impedance (D) over a thirty day period; determines an average of the derived impedance ($D_{avg}$) over the same period; and then quantifies the deviation or variation in D using:

$$D_{dev} = (D + DS)D_{avg}.$$

This value is compared against a detection threshold set, for example, to 80%. If $D_{dev}$ falls below 80%, a possible lead breach is indicated.

In the illustrative example, the CRMD also uses unipolar (U) impedance values to confirm or corroborate the breach detection. In one particular example, the CRMD measures values representative of unipolar impedance (Ui) between one or more of the lead electrodes (i) and a housing (or can) electrode of the CRMD itself. The CRMD detects any significant change in unipolar impedance (Ui) over time and, if there is no significant change, the lead breach is confirmed. Otherwise, the lead breach is disconfirmed. In this regard, a lead breach should not significantly affect unipolar impedance values. However, a change in the anatomy or physiology of the patient, such as changes due to metabolic processes, can affect both the unipolar and the derived impedances. Hence, if the unipolar and derived impedances both change, the change is likely due to anatomical or physiological changes within the patient. If only the derived impedance changes, it is likely due to a lead breach and so warnings are generated to alert the clinician, suitable diagnostic data is stored, or other appropriate steps are taken in response to the breach.

Typically, the aforementioned detection procedures are performed by the CRMD itself so it can promptly detect and respond to a lead breach. However, in at least some examples, the techniques may be performed by an external system based on impedance values received from the CRMD, such as a bedside monitor, device programmer or remote system analyzer. Moreover, whereas the examples described herein primarily exploit impedance, other related electrical parameters may be used, where appropriate, such as admittance, conductance or immittance. Where appropriate, the real component of impedance (i.e. resistance) is employed. Hence, values representative of impedance can include, e.g. impedance, admittance, conductance and/or immittance. Although the illustrative examples described herein primarily involve a CRMD having bipolar RA and RV leads where the breach point is within a middle portion of the RV lead within the RV chamber, at least some techniques are generally applicable to detecting breaches elsewhere in the RV lead, or within other leads, or within other implantable systems, such as spinal cord stimulation (SCS) systems.

BRIEF DESCRIPTION OF THE DRAWINGS

Features and advantages of the described implementations can be more readily understood by reference to the following description taken in conjunction with the accompanying drawings.

FIG. 3A and FIG. 3B provide an illustrative example of the technique for detecting lead failure of FIG. 2;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Medical System

Figure 1:
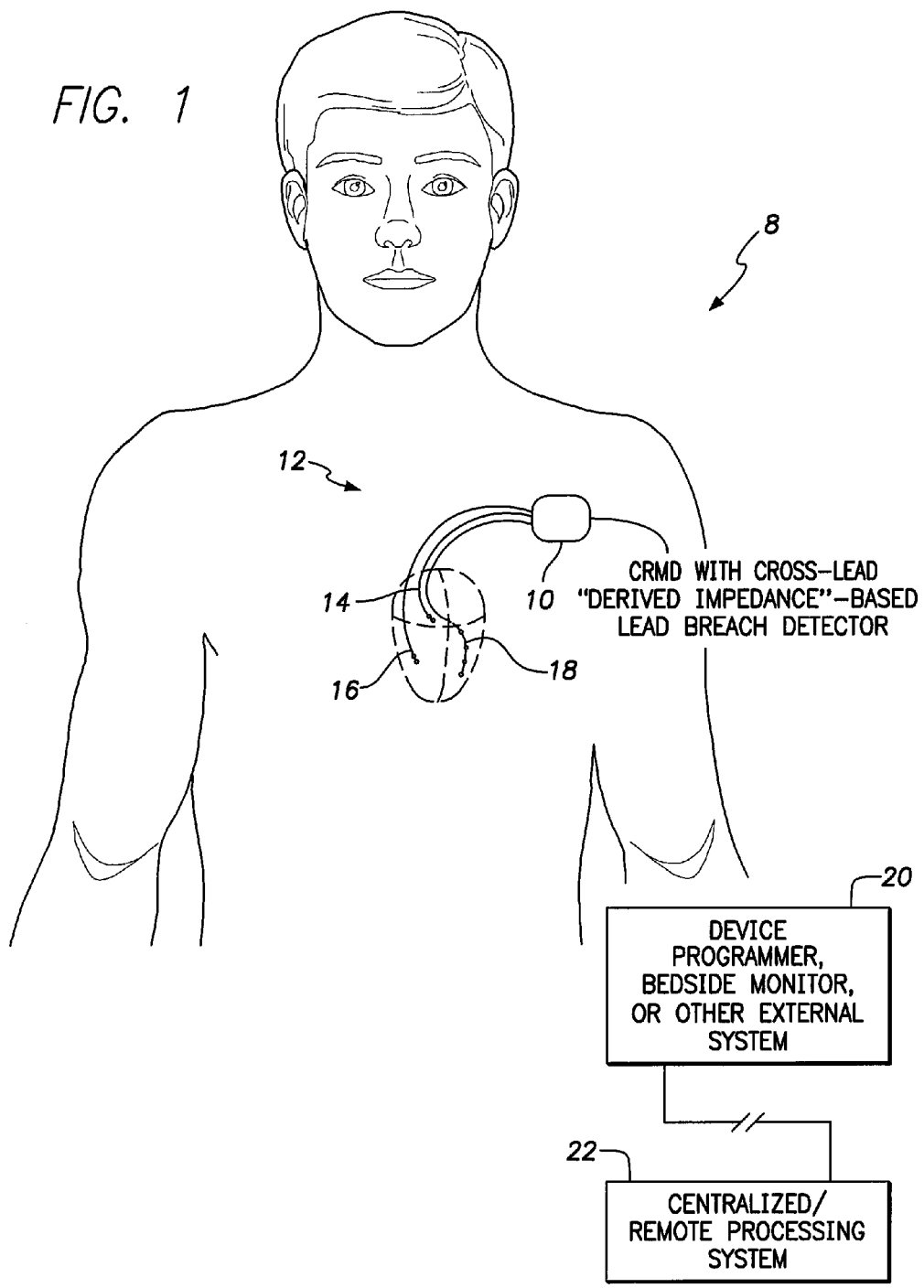
FIG. 1 illustrates pertinent components of an implantable medical system having a CRMD equipped for early detection of lead failure.

FIG. 1 illustrates an implantable medical system 8 capable of early detection of a lead breach based on derived impedance values obtained, at least in part, from cross-lead impedance measurements. That is, the CRMD is equipped with a cross-lead "derived impedance"-based lead breach detector. In the particular example of FIG. 1, implantable system 8 includes a CRMD 10 equipped with a set of leads 12 implanted on or within the heart of the patient, including a bipolar RA lead 14, a bipolar RV lead 16 and a multi-polar LV lead implanted via the coronary sinus (CS). In illustrative embodiments described below, an insulation breach within the RV lead is detected based on various bipolar, unipolar and cross-lead impedance values measured using electrodes of the RA and RV leads. The LV/CS lead is shown for the sake of completeness. Moreover, in at least some alternative implementations, a lead breach in the LV/CS lead might be detected using the general techniques described herein. Note that other leads may be employed instead of the ones specifically shown, including leads with coil electrodes mounted in or on the superior vena cava (SVC) or the left atrium (LA.) See FIG. 7 for a more complete illustration of an exemplary lead system. Note also that CRMD 10 can be any suitably-equipped implantable medical device such as a standalone pacemaker, ICD or CRT device, including CRT-D and CRT-P devices. Still further, techniques described herein may be exploited, where appropriate, within a variety of other implantable systems susceptible to lead breaches such as SCS systems. Note that the particular locations and sizes of the implanted components shown in FIG. 1 are merely illustrative and may not necessarily correspond to actual implant locations or sizes.

Using the system, if a lead breach is detected the CRMD issues warning signals to alert the patient, clinician or other caregiver, using either an internal warning device (which can be part of the CRMD) or using an external bedside monitor 20 or other suitable external system. The internal warning device may be a vibrating device, an auditory signal or a "tickle" voltage device that, in each case, provides perceptible stimulation to the patient to alert the patient so he or she may then consult a clinician. Exemplary warning/notification techniques are discussed in U.S. Pat. No. 7,272,436 to Gill et al. If a bedside monitor is provided, the monitor can receive warning signals transmitted from the implanted device and then provide audible or visual alarm signals to alert the patient or caregivers. In addition, any diagnostic information pertaining to lead breaches (or other issues) can be transferred to the bedside monitor or stored within the CRMD for subsequent transmission to an external programmer for review by a clinician or other medical professional. The clinician may then perform further tests to verify the lead breach and then surgically replace the lead, if warranted. Note that external system 20 may be networked with an internet network site or other centralized/remote processing system 22 for notifying the clinician of the lead breach or other issues. The centralized system may include such systems as Merlin.Net™ of St. Jude Medical, which may be used in conjunction with bedside monitors or similar devices such as the HouseCall™ remote monitoring system or the Merlin@Home™ systems, also of St. Jude Medical. Preferably, the CRMD itself detects a possible lead breach based on an analysis of impedance measurements obtained using its leads. However, in other implementations, the CRMD transmits its impedance measurements to external system 20, which performs the analysis or relays the data to remote system 22 for analysis. In the following examples, the CRMD performs the analysis.

Hence, FIG. 1 provides an overview of an implantable medical system equipped for early detection of a lead breach. In the following section, exemplary lead breach detection techniques will be described in detail.

Exemplary Lead Breach Detection Systems and Techniques

Figure 2:
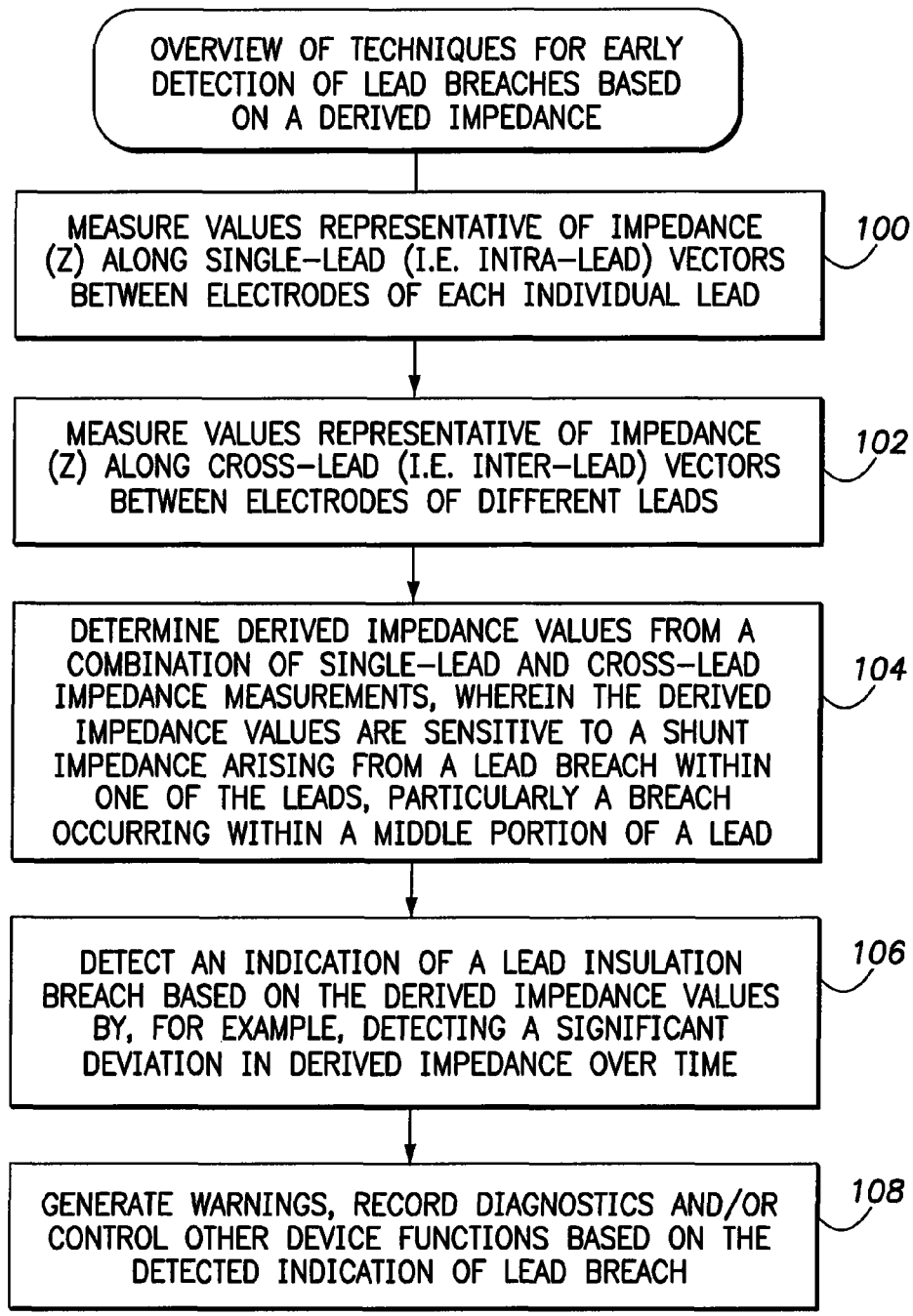
FIG. 2 provides an overview of a technique for early detection of lead failure that may be performed by the system of FIG. 1.

FIG. 2 summarizes a general method for detecting lead breaches that may be exploited by the CRMD of FIG. 1. Beginning at step 100, the CRMD measures values representative of impedance (Z) along single-lead vectors between electrodes of each individual lead, such as along a vector between the tip electrode and the ring electrode of the RV lead or along a vector between the tip electrode and the ring electrode of the RA lead. At step 102, the CRMD measures values representative of impedance along cross-lead vectors between electrodes of different leads, such as along a vector between the tip electrode of the RV lead and the ring electrode of the RA lead. As noted above, values representative of impedance can include impedance or related electrical parameters such as admittance, conductance or immittance. Where appropriate, the real component of impedance (i.e. resistance) is employed. Depending upon the particular implementation, those skilled in the art can convert between these related parameters as needed and where appropriate. Otherwise conventional impedance measurement techniques can be employed using standard impedance detection pulses. A particularly effective tri-phasic impedance detection pulse for use in measuring impedance is described in U.S. patent application Ser. No. 11/558,194 of Panescu et al., filed Nov. 9, 2006, entitled "Closed-Loop Adaptive Adjustment of Pacing Therapy based on Cardiogenic Impedance Signals Detected by an Implantable Medical Device." See, also, techniques described in U.S. patent application Ser. No. 13/007,424 of Gutfinger et al., filed Jan. 14, 2011, entitled "Systems and Methods for Exploiting Near-Field Impedance and Admittance for use with Implantable Medical Devices" and U.S. Pat. No. 8,670,820 Gutfinger et al., entitled "Near Field-Based Systems and Methods for Assessing Impedance and Admittance for use with an Implantable Medical Device." Note that, although steps 100 and 102 are shown sequentially, it should be understood that these steps may be performed concurrently (subject to the capabilities of the device itself) or in the opposite order.

At step 104, the CRMD generates, calculates or otherwise determines a derived impedance value from a combination of the measured values wherein the derived impedance is determined so as to be sensitive to a shunt impedance arising from a lead breach, particularly a breach within a middle portion of one of the leads (i.e. proximal to a ring electrode of the lead.) In the illustrative embodiments described hereinbelow, the breach occurs along a portion of the RV lead that is proximal the ring electrode of the RV lead but within the RV chamber of the heart. This is referred to as a "middle portion" of the RV lead. When the breach point is located in this middle portion (i.e. generally between the RV tip/ring electrodes and the RA tip/ring electrodes), the resulting shunt impedance reverses the direction of at least some of the cross-lead impedance vectors used to determine the derived impedance, causing a relatively significant change in the derived impedance, which allows the lead breach to be more readily detected. This is due in part to the relative anatomical locations of the RV and RA tip/ring pairs, i.e. the breach point is located substantially between the RV and RA tip/ring pairs. However, the techniques described herein can be applied to lead breaches occurring elsewhere along the RV lead, or along other leads, such as the RA or LV/CS leads. It should be understood that, if the lead breach is not generally located between a pair of tip/ring electrodes, the resulting derived impedance may be less sensitive to the resulting shunt impedance and hence the breach may not be as readily detectable. Also, if the breach is located on a different lead than the RV lead, different vectors and different equations may need to be employed other than the exemplary ones described herein (which assume a breach to the ring conductor of a bipolar RV lead within a lead system that also includes a bipolar RA lead.)

At step 106, the CRMD detects an indication of a lead breach within one of the leads (e.g. the RV lead) based on the derived impedance by, for example, detecting a significant deviation in the derived impedance over time. At step 108, the CRMD then generates warnings, records diagnostics and/or controls other device functions based on the detection of a possible lead breach. Although summarized with respect to operations performed by the CRMD, at least some of the method steps can instead be performed by an external system (such as a bedside monitor or remote system analyzer) based on impedance values transmitted from the device.

Figure 3B:
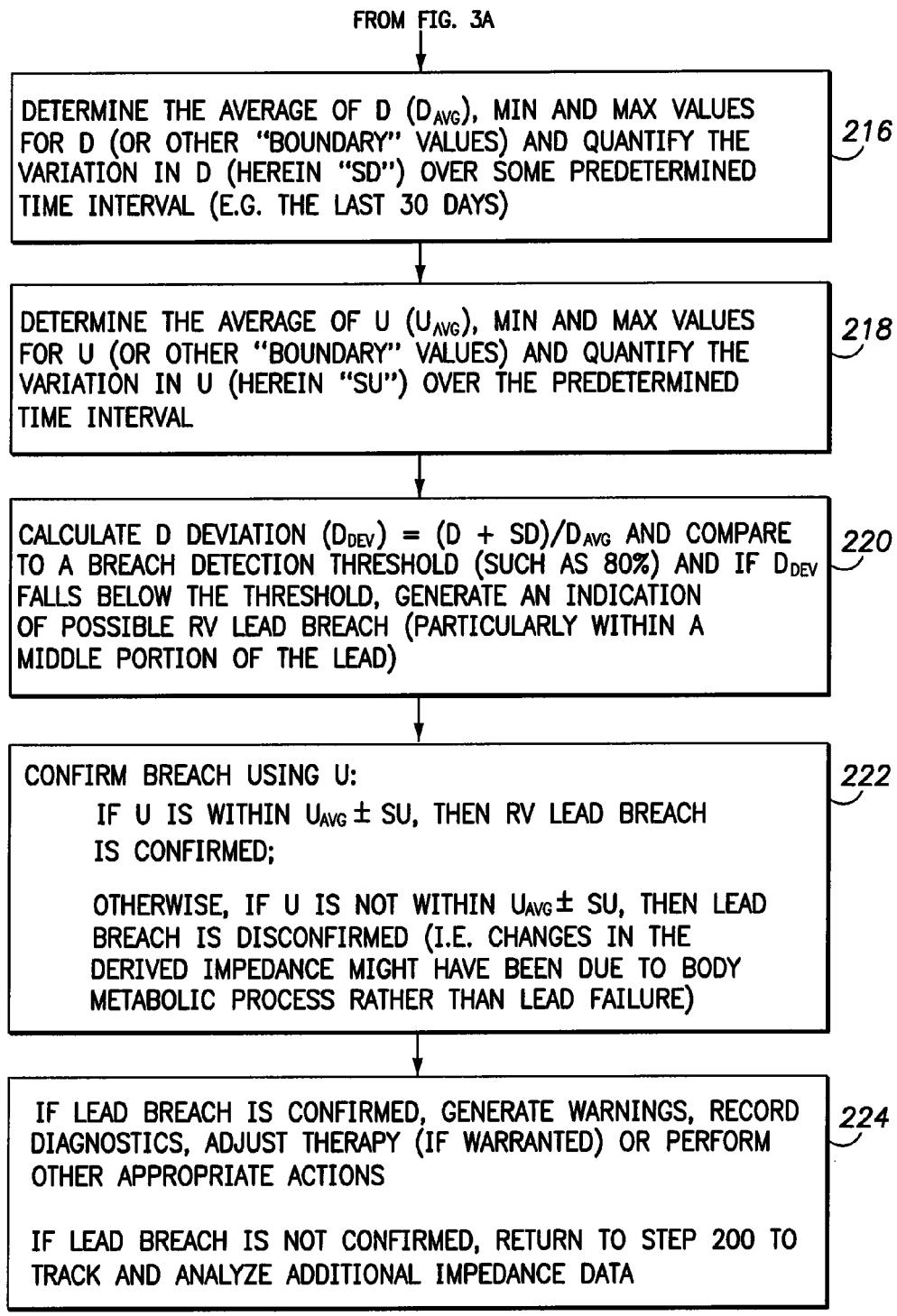
Figure 4:
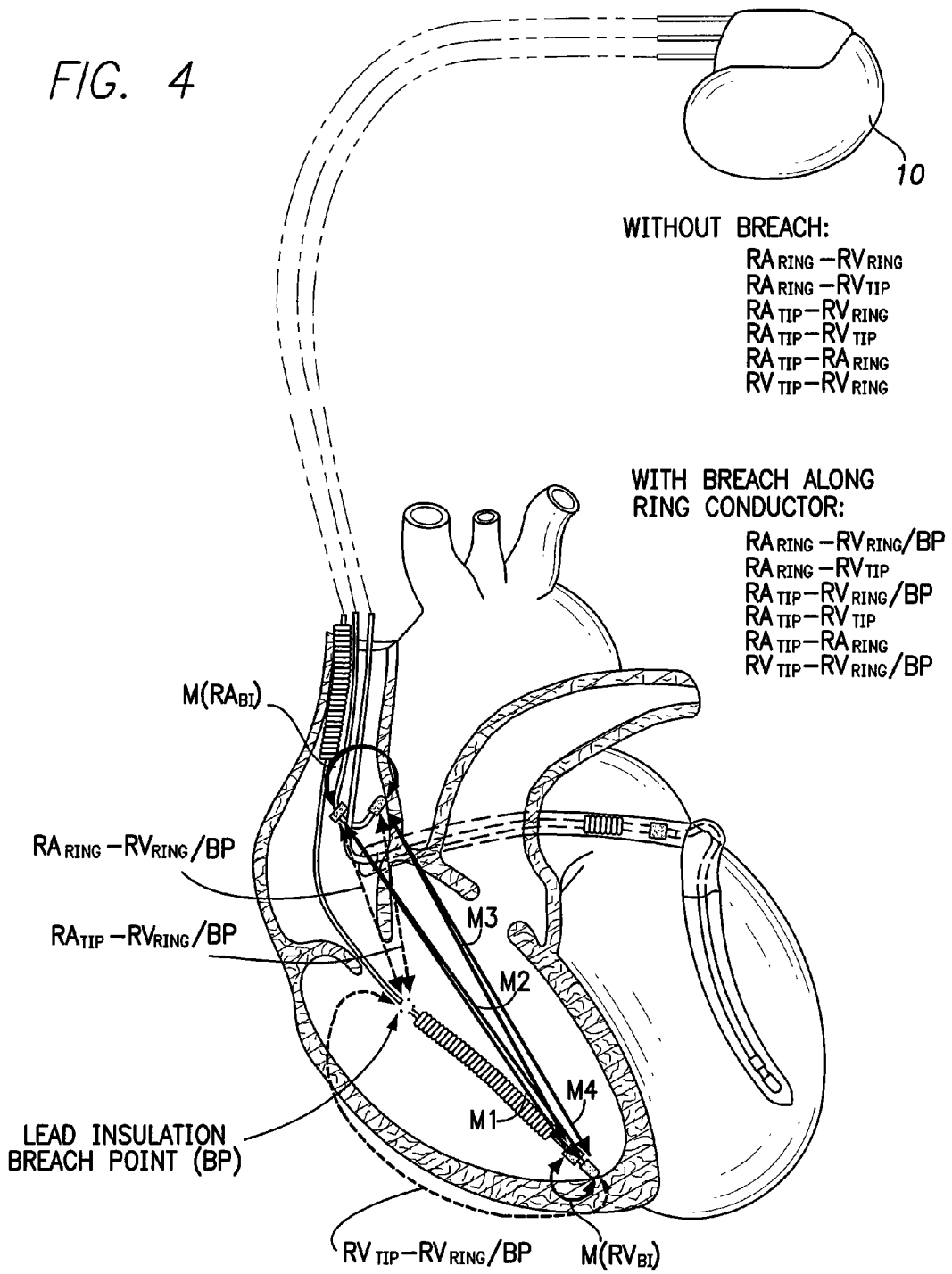
FIG. 4 illustrates exemplary impedance vectors exploited by the technique of FIGS. 3A and 3B.
Figure 5:
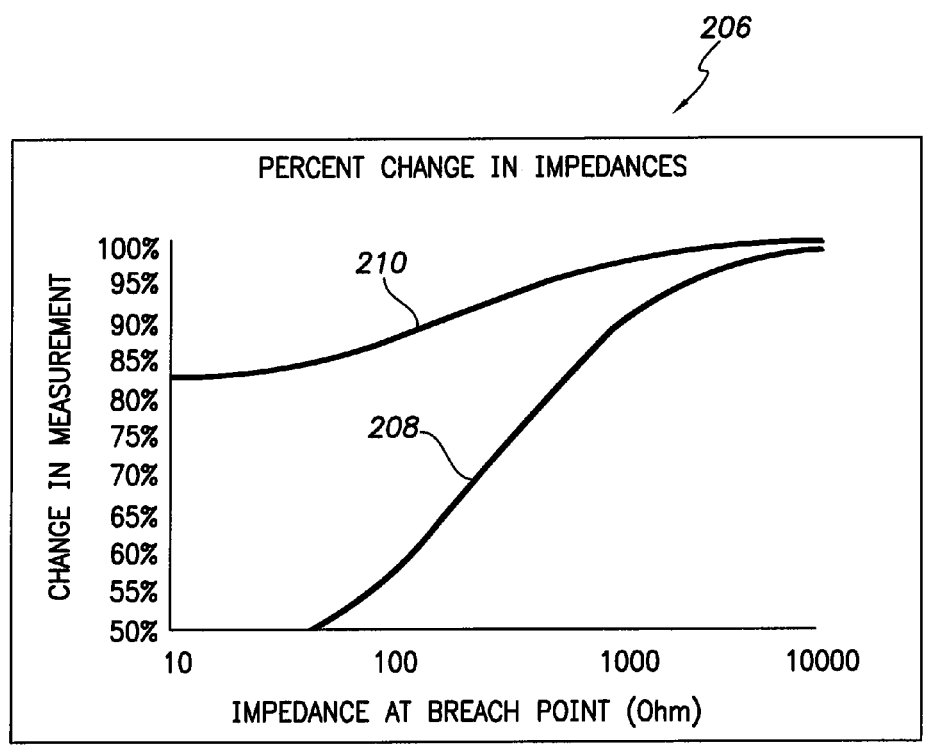
FIG. 5 is a graph comparing changes in bipolar impedance to derived impedance obtained in accordance with the method of FIG. 4.

FIGS. 3-5 illustrate an exemplary method for detecting lead breaches where a breach along a middle portion of an RV lead is detected within a lead system that also includes at least an RA lead. Beginning at step 200 of FIG. 3A, the CRMD measures single-lead (i.e. intra-lead) bipolar impedances for both the RA lead and RV lead—($M(RA_{BI})$ and $M(R_{BI})$)—where:

$$M(RA_{Bi}) = (RA_{tip} - RA_{ring}) \text{ and}$$

$$M(RV_{Bi}) = (RV_{tip} - RV_{ring}).$$

At step 202, the CRMD measures selected cross-lead (i.e. inter-lead) impedances between the RV and RA leads—M1, M2, M3, and M4—where:

$$M1 = (RA_{RING} - RV_{RING})$$

$$M2 = (RA_{RING} - RV_{TIP})$$

$$M3 = (RA_{TIP} - RV_{RING})$$

$$M4 = (RA_{TIP} - RV_{TIP})$$

These vectors are schematically shown in FIG. 4 by way of solid vector lines.

FIG. 4 also shows additional impedance paths that arise due to a breach in the RV lead at a breach point (PB) that exposes an outer coaxial ring conductor to blood or other tissues. These additional impedance vectors or paths are shown by way of dashed vector lines. $RV_{TIP} - RV_{RING}/BP$ represents the additional impedance path due to lead insulation breach exposing the RV conductor when making a bipolar RV lead impedance measurement. $RA_{TIP} - RV_{RING}/BP$ represents the additional impedance path due to the breach when making a cross-lead impedance measurement using the RA tip electrode. $RA_{RING} - RV_{RING}/BP$ represents the additional impedance path due to the breach when making a cross-lead impedance measurement using the RA ring electrode. For convenience, FIG. 4 also lists the various intra-lead and inter-lead vectors, both for the case where there is no breach and the case where there is a breach to the RV ring conductor at BP:

Without Breach:

$$RA_{ring} - RV_{ring}$$

$$RA_{ring} - RV_{tip}$$

$$RA_{tip} - RV_{ring}$$

$RA_{tip}-RV_{tip}$ $RA_{tip}-RA_{ring}$ $RV_{tip}-RV_{ring}$

With Breach Along Ring Conductor:

$RA_{ring}-RV_{ring}/BP$ $RA_{ring}-RV_{tip}$ $RA_{tip}-RV_{ring}/BP$ $RA_{tip}-RV_{tip}$ $RA_{tip}-RA_{ring}$ $RV_{tip}-RV_{ring}/BP$ Continuing with FIG. 3A, at step 204, the CRMD calculates, determines or otherwise generates a derived impedance (D) where:

$$D=SUM(M1,M2,M3,M4)-2*(M(RA_{Bi})+(M(RV_{Bi})).$$

This derived impedance value is particularly sensitive to any shunt impedance arising due to a breach at BP as demonstrated by the following analysis. For each vector, one can separate the impedances into three portions: 1) the impedance of electrode tissue interface at one end; 2) the impedance of electrode tissue interface at the other end; and 3) the impedance of the path between the two ends. Accordingly, one can separate the impedances of the aforementioned vectors as follows:

$$M1=(RA_{ring}-RV_{ring})=R(RA_{ring})+R(RV_{ring})+R(\text{Path}(RA_{ring}-RV_{ring})) \quad (1).$$

$$M2=(RA_{ring}-RV_{tip})=R(RA_{ring})+R(RV_{tip})+R(\text{Path}(RA_{ring}-RV_{tip})) \quad (2).$$

$$M3=(RA_{tip}-RV_{ring})=R(RA_{tip})+R(RV_{ring})+R(\text{Path}(RA_{tip}-RV_{ring})) \quad (3).$$

$$M4=(RA_{tip}-RV_{tip})=R(RA_{tip})+R(RV_{tip})+R(\text{Path}(RA_{tip}-RV_{tip})) \quad (4).$$

$$M(RA_{Bi})=(RA_{tip}-RA_{ring})=R(RA_{tip})+R(RA_{ring})+R(\text{Path}(RA_{tip-ring})) \quad (5).$$

$$M(RV_{Bi})=(RV_{tip}-RV_{ring})=R(RV_{tip})+R(RV_{ring})+R(\text{Path}(RV_{tip-ring})), \quad (6).$$

where R( ) refers to the real component (i.e. the resistance) of the applicable impedance (Z) measurement (assuming the frequency is sufficiently low so that impedance and resistance are similar.)

The long cross-lead path impedances can be assumed to be substantially the same (at least for the purposes of this analysis), since the paths are of about the same length and are close to each other. Hence, all long cross-lead path impedances (M1, M2, M3 and M4) can be replaced with R(Path) for simplicity. Next, summing M1 to M4, subtracting the bipolar lead impedance, and replacing with RA(Bi) and R(Bi), one obtains:

$$D=\text{Sum}(M1,M2,M3,M4)-2*(M(RA_{Bi})+(M(RV_{Bi}))) \\ =4*R(\text{Path})-2*R(\text{Path}(RA_{tip-ring}))-2*R(\text{Path}(RV_{tip-ring})) \quad (7).$$

In the presence of a lead insulation breach on the RV ring conductor wire, the additional path to the breach point (BP) will shunt parallel to the original impedance, yielding (where "(b)" refers to the breach point):

$$M1(b)=R(RA_{ring})+\{1/[R(RV_{ring})+R(\text{Path})]+1/[R(RV_{bp})+R(\text{Path}(RA_{ring}-RV_{bp}))]\}^{-1} \quad (8).$$

$$M3(b)=R(RA_{tip})+\{1/[R(RV_{ring})+R(\text{Path})]+1/[R(RV_{bp})+R(\text{Path}(RA_{tip}-RV_{bp}))]\}^{-1} \quad (9).$$

$$R(RV_{Bi})(b)=R(RV_{tip})+\{1/[R(RV_{ring})+R(\text{Path}(RV_{tip-ring}))]+1/[R(RV_{bp})+R(\text{Path}(RV_{tip}-RV_{bp}))]\}^{-1} \quad (10).$$

Again, summing M1 to M4, subtracting the bipolar lead impedance, replacing with RA(Bi) and R(Bi) and replacing the Path impedance, one obtains:

$$D=\text{Sum}(M1(b),M2,M3(b),M4)-2*(M(RA_{Bi})+(M(RV_{Bi})(b))=2*R(\text{Path})-2*R(\text{Path}(RA_{tip-ring}))+ \\ 2*\cdot\{1/[R(RV_{ring})+R(\text{Path})]+1/[R(RV_{bp})+R(\text{Path}(RA_{ring-bp}))]\}^{-1}-2*\{1/[R(RV_{ring})+R(\text{Path}(RV_{tip-ring}))]+1/[R(RV_{bp})+R(\text{Path}(RV_{tip}-RV_{bp}))]\}^{-1} \quad (11).$$

As can be seen within Equations (7) and (11), most of the impact from the bipolar lead impedances themselves is canceled, leaving the path impedance as the dominate factors. The derived impedance D can thereby be advantageously exploited to detect a lead insulation breach, particularly in circumstances where bipolar impedances would only reveal a more modest deviation.

FIG. 5 includes a graph 206 showing a plot of derived impedance 208 (as calculated using the approximation of Equation (11)) for comparison against a conventional bipolar impedance curve 210, both generated based on a lead breach at BP as shown in FIG. 4. For the example of FIG. 5, the following values were used.

$RV_{tip}=350\Omega, RV_{ring}=130\Omega, R(\text{Path}(RV_{tip-ring}))=20\Omega$ (and so RV bipolar impedance=500Ω), $RA_{tip}=350\Omega, RA_{ring}=130\Omega, RA(\text{Path}(RV_{tip-ring}))=20\Omega$ (so RA bipolar impedance=500Ω), $R(\text{Path})=100\Omega$, due to the longer distance between the electrodes of the RA lead and the RV lead, $RVR(\text{Path})$ to $BP=100\Omega$, due to a longer distance between the RV lead electrodes and the BP point, and $RAR(\text{Path})$ to $BP=50\Omega$, due to a shorter distance between the RA lead electrodes and the BP point.

In FIG. 5, the change of the impedance at BP reflects the degree of insulation breach at that abrasion point. The impedance changes were calculated and plotted as the impedance due to insulation breach as a percent of the original impedance. As can be seen, the derived impedance is more sensitive to the impedance change than the traditional bipolar lead impedance. This occurs, at least in part, because of the relative positions of the leads to each other and the position of the breach between the RA tip/ring pair and the RV tip/ring pair.

Returning to FIG. 3A, at step 212, the CRMD measures unipolar impedances ($U_i$) for some or all of the available electrodes (i) to the device can (i.e. the device housing) so that unipolar impedances can then be used to confirm or corroborate a lead breach detection. At step 214, the CRMD records and tracks values for D and U over time (such as once per day over at least a thirty day interval) to detect trends in D and U. To further reduce the impact of the physiologically induced impedance change, the impedance measurements can be made at about the same time of day and while the patient is in similar postures so that variations in impedance arising due to changes in posture or due to circadian factors do not significantly affect the measurements. Also, a number of impedance measurements can be made each day and then averaged together to provide a more robust measurement of impedance. At step 216, the CRMD derives various values for use in assessing any deviation in D such as by determining the average of D ($D_{AVG}$) and determining min and max values for D (or other "boundary" values). The CRMD then quantifies the variation in D (herein "SD") over some predetermined time interval (e.g. the last thirty days) using any suitable technique. At step 218, the CRMD likewise determines the average of U ($U_{AVG}$) for a particular unipolar vector, min and max values for U (or other "boundary" values) and then quantifies the variation in U (herein "SU") over the predetermined time interval.

At step 220, the CRMD then calculates a percentage deviation in D (herein $D_{DEV}$) where:

$$D_{DEV}=(D+SD)/D_{AVG}$$

and then compares it to a breach detection threshold, such as 80%. If $D_{DEV}$ falls below the threshold, a possible RV lead breach is thereby indicated and the device generates suitable warnings, records diagnostics, etc. At step 222, the CRMD attempts to confirm the breach by detecting any significant variation in U. For example, if U is within $U_{AVG} \pm SU$, then the RV lead breach is confirmed. Otherwise, if U is not within $U_{AVG} \pm SU$, then the lead breach is disconfirmed (i.e. changes in the derived impedance might have been due to body metabolic process rather than lead failure.) As noted above, a lead breach should not significantly affect unipolar impedance values of different vectors, only the derived impedance values. However, a change in the anatomy or physiology of the patient, such as a changes due to metabolic processes, can affect both unipolar and the derived impedances. Hence, if the unipolar and derived impedances both change, the change is likely due to anatomical or physiological changes within the patient and hence the breach is disconfirmed. If only the derived impedance changes, it is more likely due to a lead breach and so, at step 224, suitable warnings are generated to alert the clinician, suitable diagnostic data is stored, or other appropriate steps are taken in response to the breach. Following step 224, processing returns to step 200 to collect additional impedance data so that the integrity of the lead can continue to be monitored.

Where appropriate, the lead breach detection techniques described herein can be supplemented by, or corroborated by, other breach detection techniques. See, for example, techniques described in U.S. Pat. No. 7,991,472 to Levine et al., entitled "Systems and Methods for Diagnosing an Implantable Device." Also, where appropriate, to reduce the probability of a false detection, the CRMD may use additional cross-lead derived impedance values (from a different pair of leads) as reference values.

Depending upon the particular implementation, some or all of the steps of the various figures are performed by the implantable device itself. Additionally or alternatively, at least some of the steps can be performed by an external programmer or other external system based on impedance or other data measured within the patient and then transmitted to the external device. Also, although primarily described with respect to examples having a CRMD device, other implantable medical devices and lead systems may instead be equipped to exploit the techniques described. For the sake of completeness, an exemplary CRMD device will now be described, which includes components for performing the functions and steps already described.

Exemplary CRMD

Figure 6:
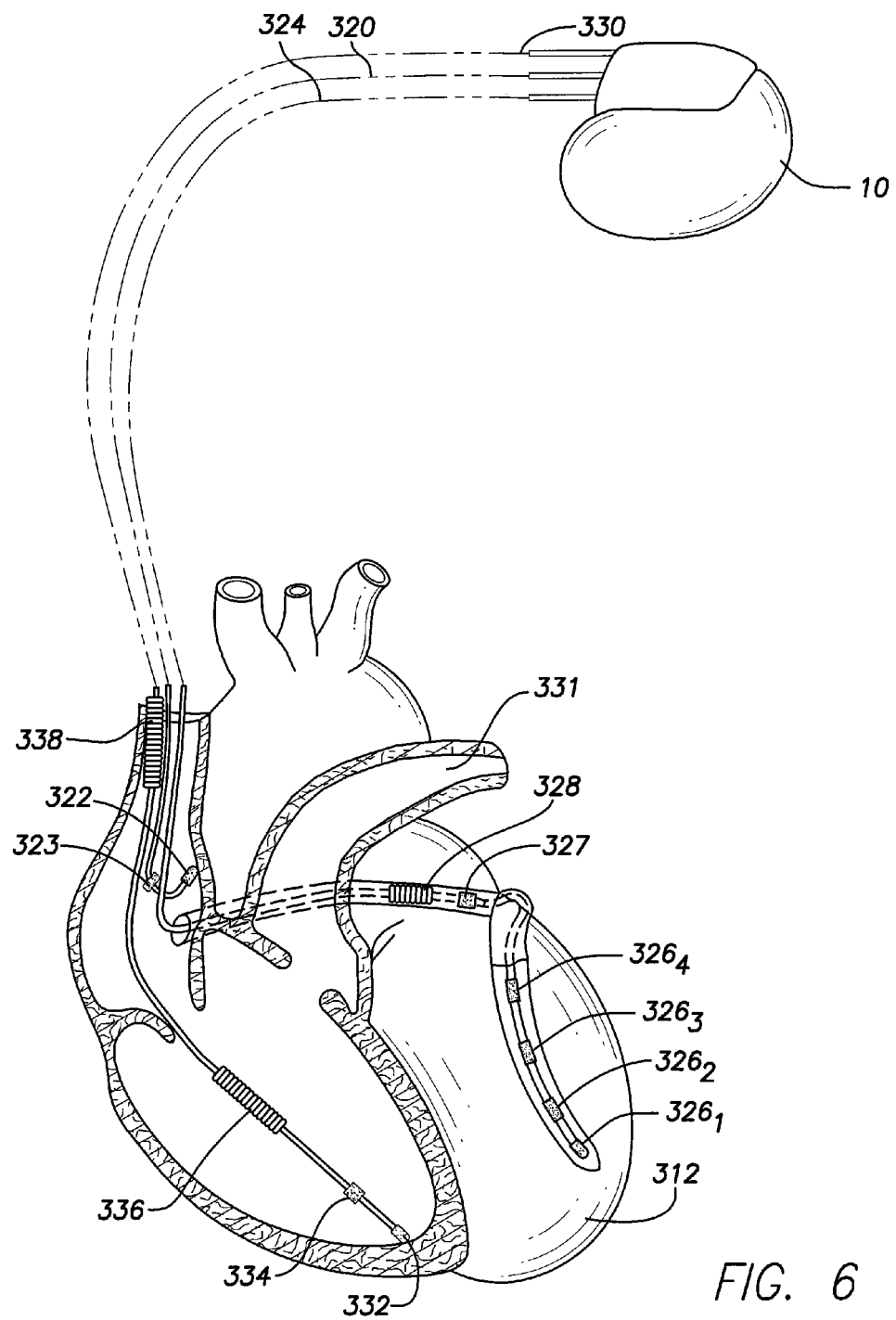
FIG. 6 is a simplified, partly cutaway view, illustrating the device of FIG. 1 along with at set of leads implanted on or in the heart of a patient.
Figure 7:
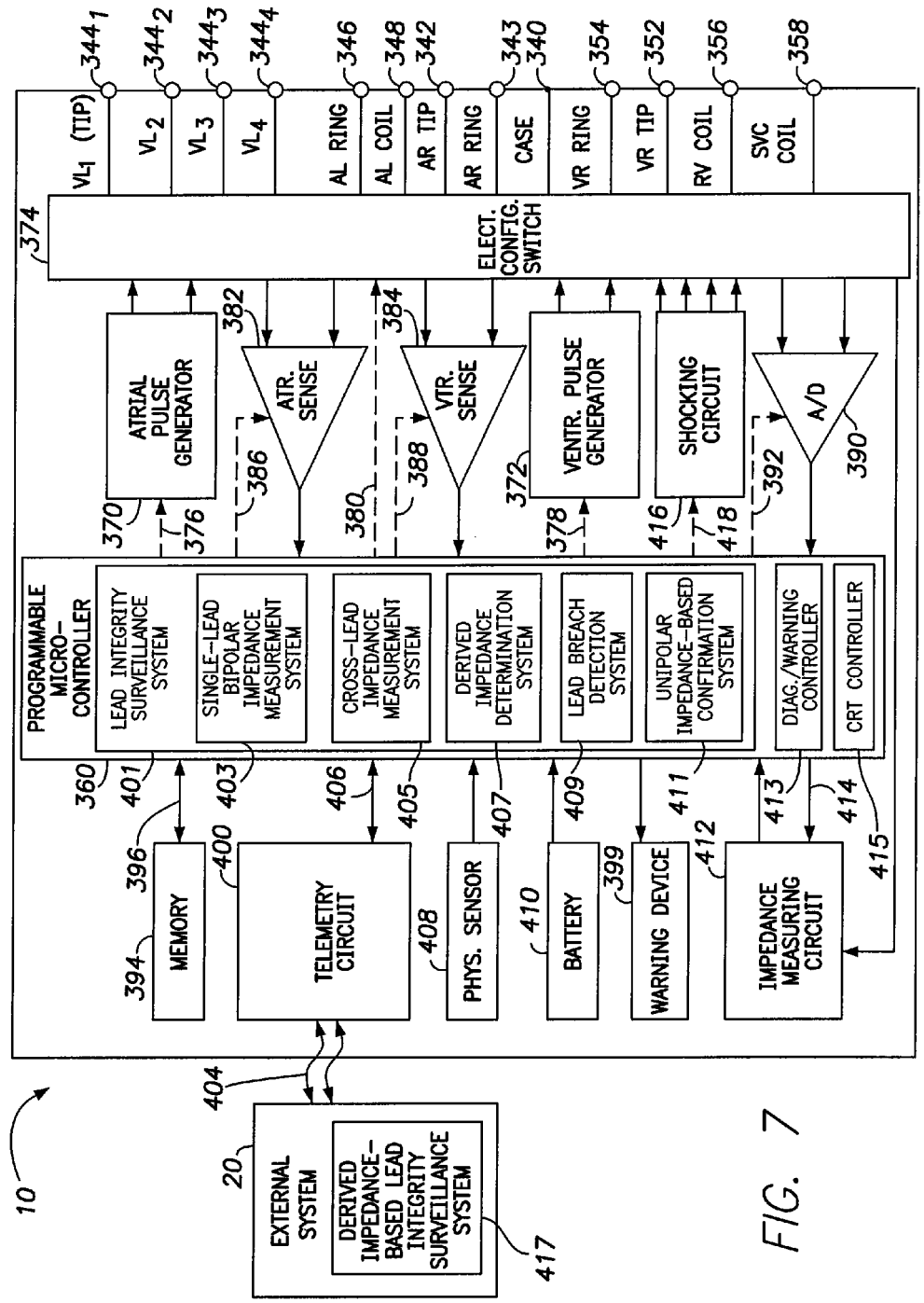
FIG. 7 is a functional block diagram of the device of FIG. 6, illustrating basic circuit elements that provide cardioversion, defibrillation and/or pacing stimulation in the heart and particularly illustrating on-board CRMD components for early detection of lead failure.

With reference to FIGS. 6 and 7, a description of an exemplary CRMD will now be provided. FIG. 6 provides a simplified block diagram of the CRMD, which is a dual-chamber stimulation device capable of treating both fast and slow arrhythmias with stimulation therapy, including cardioversion, defibrillation, and pacing stimulation, and also capable of early detection of lead breaches, as discussed above. To provide atrial chamber pacing stimulation and sensing, CRMD 10 is shown in electrical communication with a heart 312 by way of a left atrial lead 320 having an atrial tip electrode 322 and an atrial ring electrode 323 implanted in the atrial appendage. CRMD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, CRMD 10 is coupled to a multi-pole LV lead 324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 324 is designed to receive atrial and ventricular cardiac signals and to deliver left ventricular pacing therapy using a set of four left ventricular electrodes $326_1$, $326_2$, $326_3$, and $326_4$ (thereby providing a quad-pole lead such as the Quartet™ lead provided by St Jude Medical), left atrial pacing therapy using a left atrial ring electrode 327, and shocking therapy using at least a left atrial coil electrode 328. In other examples, more or fewer LV electrodes are provided. It is noted that, on present commercially-available hardware, there is often no separate electrode 327. That is, electrode $326_4$ and the "left atrial ring electrode" 327 are the same. Both electrodes are shown in the figure for the sake of completeness and generality. Moreover, although only three leads are shown in FIG. 6, it should also be understood that additional leads (with one or more pacing, sensing and/or shocking electrodes) might be used and/or additional electrodes might be provided on the leads already shown, such as additional electrodes on the RV lead.

A simplified block diagram of internal components of CRMD 10 is shown in FIG. 7. While a particular CRMD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for CRMD 10, shown schematically in FIG. 7, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, $344_1$-$344_4$, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes a left ventricular tip terminal ($VL_1$ TIP) $344_1$ and additional LV electrode terminals $344_2$-$344_4$ for the other LV electrodes of the LV lead.

The connector also includes a left atrial ring terminal ($A_L$ RING) 346 and a left atrial shocking terminal ($A_L$ COIL) 348, which are adapted for connection to the left atrial ring electrode 327 and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($V_R$ COIL) 356, and an SVC shocking terminal (SVC COIL) 358, which are adapted for connection to the right ventricular tip electrode 332, right ventricular ring electrode 334, the $V_R$ coil electrode 336, and the SVC coil electrode 338, respectively.

At the core of CRMD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 7, an atrial pulse generator 370 and a ventricular pulse generator 372 generate pacing stimulation pulses for delivery by the right atrial lead 320, the right ventricular lead 330, and/or the LV lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 382 and ventricular sensing circuits 384 may also be selectively coupled to the right atrial lead 320, LV lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables CRMD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, CRMD 10 utilizes the atrial and ventricular sensing circuits, 382 and 384, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 20. The data acquisition system 390 is coupled to the right atrial lead 320, the LV lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of CRMD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRMD 10 may be non-invasively programmed into the memory 394 through a telemetry circuit 400 in telemetric communication with the external device 20, such as a programmer, bedside monitor, personal advisory module, transtelephonic transceiver or a diagnostic system analyzer. The telemetry circuit 400 is activated by the microcontroller by a control signal 406. The telemetry circuit 400 advantageously allows intracardiac electrograms and status information relating to the operation of CRMD 10 (as contained in the microcontroller 360 or memory 394) to be sent to the external device 20 through an established communication link 404. CRMD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV delay, VV delay, etc.) at which the atrial and ventricular pulse generators, 370 and 372, generate stimulation pulses. While shown as being included within CRMD 10, it is to be understood that the physiologic sensor 408 may also be external to CRMD 10, yet still be implanted within or carried by the patient. A common type of rate responsive sensor is an activity sensor incorporating an accelerometer or a piezoelectric crystal, which is mounted within the housing 340 of CRMD 10. Other types of physiologic sensors are also known, for example, sensors that sense the oxygen content of blood, respiration rate and/or minute ventilation, pH of blood, ventricular gradient, etc.

The CRMD additionally includes a battery 410, which provides operating power to all of the circuits shown in FIG. 7. The battery 410 may vary depending on the capabilities of CRMD 10. If the system only provides low voltage therapy, a lithium iodine or lithium copper fluoride cell typically may be utilized. For CRMD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, appropriate batteries are employed.

As further shown in FIG. 7, CRMD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement and for early detection of lead failure as discussed above; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 412 is advantageously coupled to the switch 474 so that any desired electrode or combination of electrodes may be used.

In the case where CRMD 10 is intended to operate as an ICD device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules or higher), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules or more), delivered asynchronously (since R-waves may be too disorganized), and pertaining exclusively to the treatment of fibrillation. Accordingly, the microcontroller 360 is capable of controlling the synchronous or asynchronous delivery of the shocking pulses. An internal warning device 399 may be provided for generating perceptible warning signals to the patient via vibration, voltage or other methods.

Insofar as lead surveillance is concerned, the microcontroller includes a lead integrity surveillance system 401 operative to detect possible lead breaches or other lead integrity issues based, at least in part, on derived impedance values exploiting cross-lead impedance measurements. In this example, surveillance system 401 include single-lead bipolar impedance measurement system 403 operative to measure or input signals representative of impedance along single-lead (intra-lead) vectors between electrodes of individual leads. A cross-lead impedance measurement system 405 is operative to measure or input signals representative of impedance along cross-lead (inter-lead) vectors between electrodes of different leads. A derived impedance determination system 407 is operative to determine a derived impedance value from a combination of the measured signals wherein the derived impedance is sensitive to a shunt impedance arising from a lead breach within a middle portion of one of the leads. A lead breach detection system 409 is operative to detect a lead breach within the middle portion of one of the leads based on the derived impedance. A unipolar impedance-based confirmation system 411 is operative to measure or input unipolar impedance signals for confirming or corroborating any detection of a lead breach made by detection system 409. A diagnostics/warning controller 413 controls the recording of diagnostics and/or the generation of warning signals in response to detection of possible lead breaches or other issues. If the device is equipped to deliver CRT, a CRT controller 415 controls the CRT.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

At least some of the techniques described herein may be performed by, or under the control of, an external device. Accordingly, external device 20 is shown to include a derived impedance-based lead integrity surveillance system 417 operative to perform the analysis of system 401 of the CRMD based on signals or data received from the CRMD. In general, any of the components shown within the microcontroller 360 may have corresponding components within the external device.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for implant within a patient having a lead system with at least two leads each with a plurality of electrodes, the method comprising:
    measuring values representative of impedance along single-lead vectors between electrodes of each individual lead;
    measuring values representative of impedance along cross-lead vectors between electrodes of different leads;
    determining derived impedance values from a combination of the values representative of impedance measured along the single-lead vectors and the values representative of impedance measured along the cross-lead vectors, wherein the derived impedance values are sensitive to a shunt impedance arising from a lead breach within one of the leads; and
    detecting an indication of a lead breach within one of the at least two leads based on the derived impedance values.

2. The method of claim 1 wherein the lead breach is located at a position along one of the leads so that at least one impedance vector reverses direction as a result of the shunt impedance arising from the breach.

3. The method of claim 2 wherein the lead system includes first and second bipolar leads, each with a tip/ring electrode pair, and wherein the breach is located at a position along one of the leads generally between the tip/ring pair of the first lead and the tip/ring pair of the second leads.

4. The method of claim 1 wherein the lead system includes a right ventricular (RV) bipolar lead and a right atrial (RA) bipolar lead and wherein measuring values representative of impedance along single-lead vectors includes:
    measuring values $M(RA_{Bi})$ representative of impedance between tip and ring electrodes of the RA lead (RA tip–RA ring); and
    measuring values $M(RV_{Bi})$ representative of impedance between tip and ring electrodes of the RV lead (RV tip–RV ring).

5. The method of claim 4 wherein measuring values representative of impedance along cross-lead vectors includes:
    measuring values (M1) representative of impedance between the RA tip and RV ring electrodes;
    measuring values (M2) representative of impedance between the RA ring and RV tip electrodes;
    measuring values (M3) representative of impedance between the RA tip and RV ring electrodes; and
    measuring values (M4) representative of impedance between the RA tip and RV tip electrodes.

6. The method of claim 5 wherein determining derived impedance values includes determining a derived impedance (D) as a sum of the cross-lead impedance values (M1, M2, M3, M4) less twice the sum of the single lead impedance values ($M(RA_{Bi})$, $M(RV_{Bi})$).

7. The method of claim 6 wherein detecting an indication of a lead breach based on derived impedance values includes detecting any change in the derived impedance (D) over time and comparing the change to a threshold indicative of a possible lead breech.

8. The method of claim 7 wherein detecting any significant change in the derived impedance (D) over time includes:
    determining a variation (SD) in the derived impedance (D);
    determining an average of the derived impedance (Davg); and
    determining a sum of D and DS divided by Davg.

9. The method of claim 8 wherein comparing the change in derived impedance (D) to a threshold indicative of a possible lead breech includes comparing the amount of change ((D+SD)/Davg) to a threshold set based on a predetermined percentage.

10. The method of claim 9 wherein the predetermined percentage is no greater than 80%.

11. The method of claim 8 wherein the average is a running average determined over a predetermined amount of time.

12. The method of claim 11 wherein the predetermined amount of time is at least thirty days.

13. The method of claim 1 further including confirming an indication of lead breach based on unipolar impedance values measured using the leads and a housing of the implantable medical device.

14. The method of claim 13 wherein confirming an indication of lead breach based on unipolar impedance values includes:
    measuring values representative of unipolar impedance (U) between one or more of the electrodes and the housing of the device;
    detecting any significant change in unipolar impedance (U) over time; and
    if there is no significant change in unipolar impedance (U), then generating an indication that the lead breach is confirmed;
    otherwise generating an indication that the lead breach is disconfirmed.

15. The method of claim 14 wherein detecting any significant change in unipolar impedance (U) over time includes:
    determining a variation (SU) in the unipolar impedance (U);
    determining an average of the unipolar impedance (Uavg); and
    determining whether the unipolar impedance (U) is not between Uavg+SU and Uavg−SU.

16. The method of claim 1 wherein all of the steps are performed by the implantable medical device.

17. The method of claim 1 wherein at least some of the steps are performed by an external device based on values received from the implantable medical device.

18. A system for use with an implantable medical device for implant within a patient having a lead system with at least two leads each with a plurality of electrodes, the system comprising:
    a single-lead impedance measurement system operative to measure values representative of impedance along single-lead vectors between electrodes of each individual lead;
    a cross-lead impedance measurement system operative to measure values representative of impedance along cross-lead vectors between electrodes of different leads;
    a derived impedance determination system operative to determine a derived impedance value from a combination of the values measured by the single-lead impedance measurement system and the values measured by the cross-lead measurement system, wherein the derived impedance values are sensitive to a shunt impedance arising from a lead breach within one of the leads; and
    a lead breach detection system operative to detect an indication of a lead breach within one of the leads based on the derived impedance values.

19. A system for use with an implantable medical device for implant within a patient having a lead system with at least two leads each with a plurality of electrodes, the system comprising:

means for measuring values representative of impedance along single-lead vectors between electrodes of each individual lead;

means for measuring values representative of impedance along cross-lead vectors between electrodes of different leads;

means for determining a derived impedance value from a combination of the values representative of impedance measured along the single-lead vectors and the values representative of impedance measured along the cross-lead vectors, wherein the derived impedance values are sensitive to a shunt impedance arising from a lead breach within one of the leads; and means for detecting an indication of a lead breach within one of the leads based on the derived impedance values.

* * * * *